Figure 1:
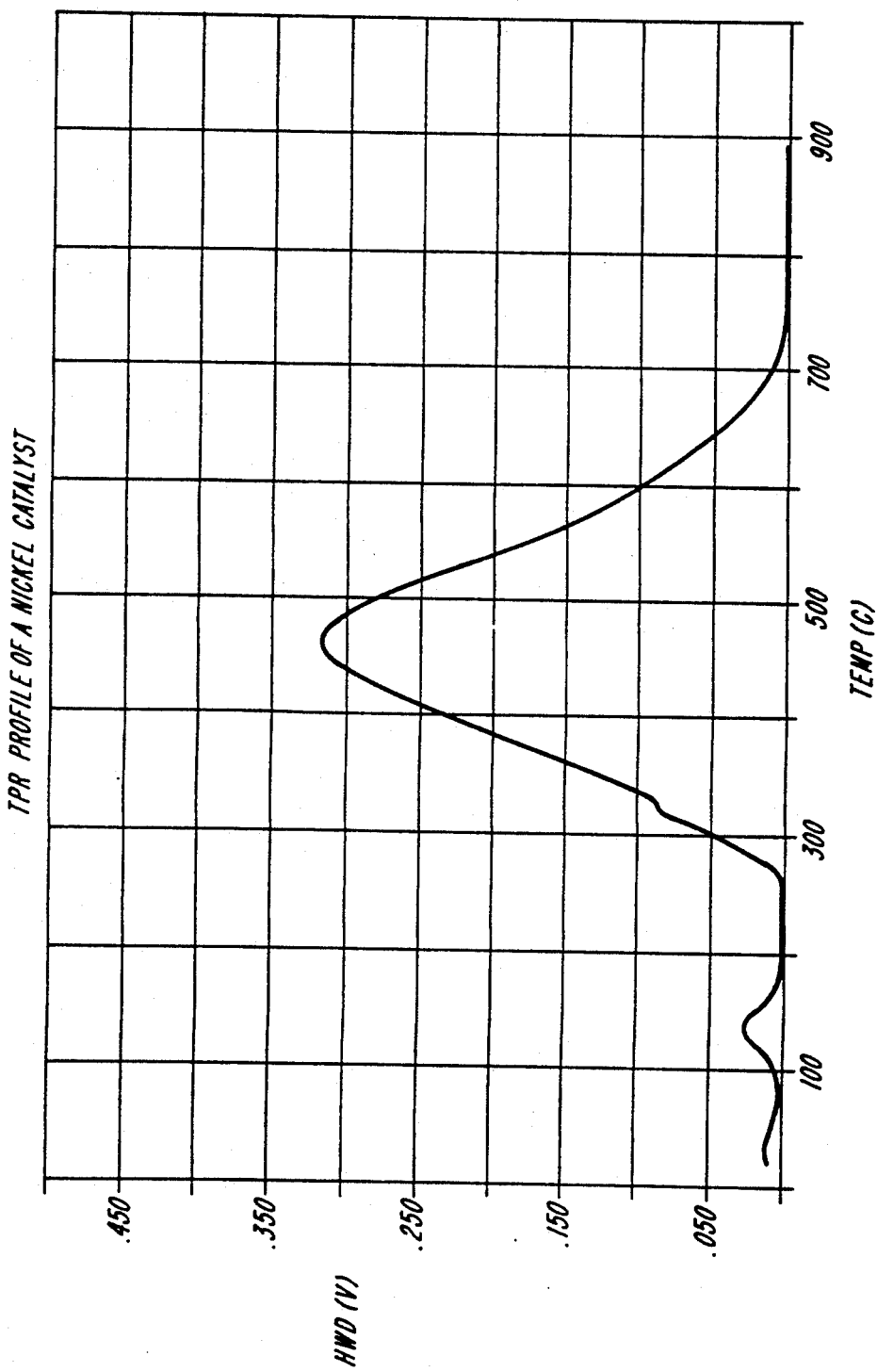

United States Patent [19]

Borninkhof et al.

[11] Patent Number: 5,235,108

[45] Date of Patent: Aug. 10, 1993

[54] PROCESS FOR PREPARING SECONDARY ALKYLAMINE

[75] Inventors: Frederik Borninkhof, Nieuwegein; Eugene G. M. Kuijpers, Apeldoorn; Pieter H. Berben, Maarn, all of Netherlands

[73] Assignee: Engelhard De Meern B.V, Strijkviertel, Netherlands

[21] Appl. No.: 837,562

[22] Filed: Feb. 18, 1992

Related U.S. Application Data

[63] Continuation of Ser. No. 483,564, Feb. 22, 1990, abandoned.

[30] Foreign Application Priority Data

Feb. 24, 1989 [NL] Netherlands ............ 8900465

[51] Int. Cl.$^5$ ............................................. C07C 209/00
[52] U.S. Cl. ............................ 564/490; 564/415; 564/458; 564/491
[58] Field of Search ............ 502/337; 564/490, 491, 564/415, 458; 260/404.5

[56] References Cited

U.S. PATENT DOCUMENTS

| B 391,828 | 4/1976 | Boettger et al. ............ 260/563 |
| 2,165,515 | 7/1939 | Schmidt ........................ 260/583 |
| 3,152,998 | 10/1964 | Moss ............................. 252/470 |
| 3,673,251 | 6/1972 | Frampton et al. ............ 260/563 D |
| 4,263,225 | 4/1981 | Carter et al. ................... 564/490 |

FOREIGN PATENT DOCUMENTS

| 1941290 | 3/1971 | Fed. Rep. of Germany . |
| 3048832 | 9/1981 | Fed. Rep. of Germany . |
| 3216384 | 11/1983 | Fed. Rep. of Germany . |
| 77367 | 1/1962 | France . |
| 4947303 | 5/1974 | Japan . |
| 542609 | 1/1942 | United Kingdom . |
| 0759291 | 10/1956 | United Kingdom . |
| 1323351 | 7/1973 | United Kingdom . |

OTHER PUBLICATIONS

Areshizde et al, "Hydrogenation of Autonitrite, etc." Soobsch. Akad. Nauk Gruz. SSR 1976 83(2), 373-6 abstracted in Chem. Abst. vol. 85, 22 Nov. 76, p. 486, Abstract No. 159302b.

Chemical Abstract, vol. 70, 22nd Jun. 1969, p. 273, abstract No. 100057n, Columbus OH, V. P. Vetrov et al, "Effect of some additives on the activity of a mixed nickel-copper catalyst on a carrier during the hydrogenation of glucose".

Chemical Abstract, vol. 101, 27th Aug. 1984, p. 604, abstract No. 72260m, Columbus, OH HU-A-29-745; 28 Feb. 1984, (Peti Nitrogenmuvek).

Chemical Abstract, vol. 81, 11th Nov. 1974, p. 474, abstract No. 119919u, Columbus OH & JP-A-74 47 303 (Mitsubhishi Chemical Industries Co., Ltd.) 08 May 1974.

"Catalytic Hydrogenation", L. Volf and J. Pasek, vol. 27, pp. 105-144, Elsevier, 1986.

"Temperature Programmed Reduction", Nicholas W. Hurst, et al, Catal. Rev. Sci. Eng. vol. 24(2), pp. 233-309 (1982).

Primary Examiner—Richard L. Raymond
Assistant Examiner—P. O'Sullivan
Attorney, Agent, or Firm—Weingarten, Schurgin, Gagnebin & Hayes

[57] ABSTRACT

This invention relates to a process for preparing secondary alkylamine by selective hydrogenation of alkylnitrile using a nickel-containing catalyst which contains copper as promoter, said catalyst having a selectivity, as herein defined, of not more than 8.

12 Claims, 4 Drawing Sheets

PROCESS FOR PREPARING SECONDARY ALKYLAMINE

This application is a continuation of application Ser. No. 07/483,564, filed Feb. 22, 1990, abandoned.

This invention relates to a process for preparing secondary alkylamine by converting alkylnitrile in the presence of a nickel-containing catalyst.

The preparation of secondary amines from alkylnitrile is known per se and is generally effected by catalyzed hydrogenation. Use is then made of either supported or unsupported hydrogenation catalysts, such as nickel or cobalt catalysts.

The reactions occurring in the preparation of secondary alkylamines from alkylnitriles can be distinguished broadly into two groups, namely hydrogenation reactions and condensation reactions.

During the preparation hydrogenation of the nitrile group to primary amine occurs, optionally in combination with a partial saturation of unsaturated groups in the alkyl skeleton, if present. Besides, condensation and deammoniation reactions occur in which the primary amines are converted to secondary and tertiary amines. If desired, unsaturation still present in the alkyl skeleton can be removed by continued hydrogenation.

A survey of the catalysts used for the hydrogenation of nitriles is given in the article by L. Volf and J. Pasek in "Catalytic hydrogenation" (Ed. L. Cerveny), Studies in Surface Science and Catalysis, vol. 27, pages 105-144, Elsevier, 1986.

This article shows that during the hydrogenation of nitriles different products are formed. In addition to primary amines, there are formed secondary and tertiary amines. The selectivity of the reaction towards the desired amines can in a way be controlled by the proper selection of reaction conditions, such as pressure, temperature, and the presence or absence of ammonia and other additives. Nevertheless, it proves difficult in practice to adjust the reaction conditions so that not only a high selectivity, but also a sufficiently high reaction velocity is obtained.

U.S. Pat. No. 2,165,515, corresponding to French patent 773,367, discloses, inter alia, the use of nickel, copper and cobalt catalysts for the preparation of aliphatic amines, more in particular primary amines.

U.S. Pat. No. 3,673,251 describes a cyclic process for the reductive amination of nitrile to form secondary or tertiary amines. The specification indicates that any hydrogenation catalyst can be used. Different types of catalysts are mentioned, including copper-nickel carbonate. In the examples only palladium or cobalt is used.

German patent publication 32 16 384 describes the preparation of neopentylamine, a primary amine, from pivalonitrile using a hydrogenation catalyst.

German patent publication 30 48 832 describes the preparation of a secondary amine with nitrogen groups in the chain. Catalysts used are, inter alia, Ni-Cu chromite and Co-Cu chromite. The selectivity and yield are very low.

British patent 1,323,351 discloses the preparation of secondary alkylamines by using a nickel or cobalt catalyst in a first reactor and a copper catalyst in a second reactor. It is very laborious, and therefore economically unattractive, that two different catalysts must be used in two separate process steps.

The object of this invention is, inter alia, to provide a process for preparing secondary alkylamine using a nickel catalyst, starting from alkylnitrile, with improved selectivity, while retaining the activity. Another object of the invention is to provide a process for selectively preparing secondary unsaturated alkylamine, more in particular secondary unsaturated fatty acid amine, from an unsaturated alkylnitrile. The fatty nitrile starting material for the preparation of fatty acid amine is, optionally, derived from fatty acid having 12-22 carbon atoms.

This invention is characterized in that the selective hydrogenation of alkylnitrile is carried out using a nickel-containing catalyst which contains copper as promoter, said catalyst having a selectivity, as herein defined, of not more than 8.

Surprisingly, it has been found that the use of copper as promoter in the nickel catalyst for the preparation of secondary alkylamine (dialkylamine) from alkylnitrile gives an improved selectivity without a decrease of activity.

According to a preferred embodiment of the invention a catalyst is used which contains cobalt as copromoter. It has actually been found that the use of cobalt gives a further improvement of the selectivity.

It is of essential importance for the catalyst to have a selectivity, as will hereinafter be defined, of not more than 8, more in particular not more than 6.5. As appears from the definition of selectivity, a value of 0 is the optimal value.

The selectivity of the catalyst is defined on the basis of the conversion of 500 g tallow nitrile in secondary amines. Tallow nitrile consists mainly of nitrile having 16 or 18 carbon atoms, a large portion of the $C_{18}$-chains being monounsaturated. An analysis characteristic of tallow nitrile to be used for the determination of the selectivity gives an iodine number of 50-60, a content of free fatty acids of less than 0.15 wt. %, a content of amide of less than 0.5 wt. %, and a water content of less than 0.1 wt. %.

The amount of catalyst used for the determination of the selectivity depends on the composition of the catalyst.

When using catalysts having a molar ratio of nickel/promoter(s) $\geq 70/30$, there is used per 500 g tallow nitrile an amount of catalyst corresponding to 17 mmol nickel, i.e. about 1 g nickel calculated as a metal. This means, therefore, that the total amount of metal, namely nickel and (co)promoters together, is higher. For catalysts having a lower nickel/promoter ratio there is introduced into the reaction mixture an amount of catalyst corresponding to a total amount of metal {nickel+promoter(s)} of 24 mmol.

For the purpose of this invention selectivity is defined as the content (wt. %) of trialkylamines at the time that the reaction mixture contains exactly 5.0 wt. % monoalkylamines and essentially no unconverted nitriles, the total reaction time to reach this, not being allowed to exceed 270 min.

The selectivity determination is carried out as described under "Performance" in the examples.

The analysis of the reaction mixture is carried out as follows.

The reaction mixture is analyzed for contents of respectively monoalkylamines, dialkylamines, and trialkylamines by means of an acid-base titration of amines with hydrochloric acid.

Three titrations are required to determine the final product composition. In the first titration both monoalkylamines and di- and trialkylamines are analyzed. During the second titration salicylaldehyde is added to the reaction mixture to mask the monoalkylamines so that only dialkylamines and trialkylamines are analyzed. The third titration is finally effected with addition of acetic anhydride, which reacts with the monoalkylamines and dialkylamines so that in this titration only the trialkylamines are titrated.

By combining the above analyses the final product composition can be calculated.

An essential aspect of the process according to the invention is therefore that the hydrogenation should be selective This means that the process should result in that at least 85% of the alkylnitrile is converted to secondary alkylamine.

It is also important that the activity should be sufficient. This is expressed in the requirement that in the procedure for the determination of the selectivity, as referred to above, the conversion must be so rapid that the content of primary amine of 5 wt. % must be reached within 270 min. If this is not realized, then the catalyst is not satisfactory.

Copper has already been used as promoter in nickel catalysts for suppressing hydrogenolysis reactions which may strongly occur in the presence of nickel hydrogenation catalysts. Such a reaction not only leads to the breaking of the carbon skeleton of the compound to be hydrogenated, but often also to the deposition of carbon. The use of copper suppresses the hydrogenolysis so that a better efficiency of the reaction is obtained. The use of copper as promoter, however, generally has the disadvantage of decreasing the activity of the catalyst.

The nickel induced hydrogenolysis and carbon formation, however, hardly, if at all, occur under the reaction conditions for the preparation of secondary alkylamine by conversion of alkylnitrile. It will therefore not be considered to include copper as a promoter in a nickel-based catalyst for the preparation of secondary alkylamine from alkylnitrile, as this is expected to result in a decreased activity.

Surprisingly, it has been found, however, that the use of copper as promoter in a nickel catalyst gives an increased selectivity of the reaction towards the secondary amine. Moreover, it has been found that the activity of the catalyst does not decrease, but even slightly increases.

An additional advantage of using the copper promoted nickel catalyst lies in the fact that the catalyst can be used at lower temperatures, which results in a lower reaction velocity of the hydrogenation of the unsaturated carbon-carbon bonds. Consequently, it is possible with the process according to the invention to prepare unsaturated secondary alkylamines with a good selectivity.

For a good effect of the catalyst it is important that the copper should be effectively present as promoter, which means that at least part of the copper is present in a mixed phase with the nickel. In general, 5–100% of the copper is in direct contact with the nickel. To determine the presence of a direct contact, or an alloy, the TPR analysis can be used (see N. W. Hurst et al. Catal. Rev.-Sci. Eng., Vol. 24(2), pages 233–309 (1982)). Temperature programmed reduction (TPR) means that the $H_2$ consumption during reduction of the catalyst precursor is determined in dependence on the temperature.

In case there is no contact between copper and nickel, there are at least two temperatures at which the $H_2$ consumption shows a maximum; one of these maxima corresponds to the reduction to nickel and a second corresponds to the reduction to copper. As soon as there is direct contact of nickel and copper, the TPR pattern shows one or more maxima which do not correspond to pure nickel or to pure copper either, but may be an indication of the formation of a copper/nickel mixed phase.

The presence of such a copper/nickel mixed phase or alloy can also be demonstrated by means of the IR absorption spectra of CO adsorbed on the catalyst. It is known that CO adsorbed on pure copper will easily desorb, while CO adsorbed on pure nickel cannot be desorbed by evacuation at room temperature. An absorption band of CO in the IR spectrum obtained after evacuation of the catalyst is therefore to be attributed to CO adsorbed on "nickel-like" sites.

On pure nickel catalysts irreversibly adsorbed CO induces two absorption bands. The band having a maximum at 2045 $cm^{-1}$ is attributed to linearly bound CO, while the other band having a maximum at 1950 $cm^{-1}$ is attributed to bridged-bound CO. Dalmon et al, Surface Sci., 50 (1975), page 95, have observed that the maxima of the two bands were shifted to lower frequencies, if a nickel on silica gel catalyst was alloyed with copper. In addition to the frequency shift, they also observed a decrease of the intensity in both bands with increasing copper content. The band attributed to the bridged-bound CO showed a considerably larger reduction than the other band. This was explained by the fact that a larger number of nickel atoms per binding site is required for bridged-bound CO than for linearly bound CO. At copper contents above 50% the band of bridged-bound CO fully disappeared.

According to a further preferred embodiment of the invention a catalyst is used which contains cobalt as second promoter. The fact is that it has surprisingly been found that such a catalyst with copper as promoter and cobalt as copromoter shows a further improved selectivity.

The catalyst used according to the invention can be prepared in different ways. Suitable methods are the precipitation of copper on a catalyst precursor already containing nickel, or vice versa, and the simultaneous precipitation of copper and nickel. The cobalt as copromoter, if used, can be applied to the catalyst at any suitable moment.

According to a preferred embodiment of the invention a catalyst on carrier is used, said carrier preferably consisting of a metal oxide or a mixture of metal oxides. Suitable carrier materials are, e.g., alumina, silica, kieselguhr, and combinations thereof.

When supported catalysts are used, these are prepared, e.g., by precipitation of the active ingredients or precursors thereof on a preformed carrier, by coprecipitation or by impregnation of the preformed carrier with a solution of the active ingredients or precursors thereof. The precipitation occurs in a manner known in the state of the art, e.g., by injection of an ingredient causing precipitation, such as lye or a soda solution, in a solution or slurry of (a precursor of) the carrier, which also contains precursors of the active ingredients. The impregnation occurs, e.g., by contacting an amount of a solution of the active ingredients or precursors thereof with the carrier. The amount of liquid may be an excess, so that after saturation of the carrier with the solution the remaining liquid is removed, after which the impregnated carrier is dried. It is also possible to contact just as much liquid with the carrier as corresponds to the pore volume of the carrier, so that the carrier fully takes up the liquid. Then the thus obtained catalyst precursor is dried.

After drying the catalyst precursor this is calcined and completely or partly reduced.

In general, the metal components or precursors thereof can be applied simultaneously or successively. When the copper promoter is used, it is important, however, that this should be applied in a form in which the promoting effect can be expressed. This is generally not the case when there is no direct contact in the active catalyst between at least part of the copper and the nickel.

When a carrier is used, the amount thereof, based on the catalyst, preferably ranges from 5 to 95 wt. %, more in particular from 15 to 60 wt. %.

The content of nickel, based as total Ni when compared with the content of total Ni and total promoter(s) together, generally ranges from 1 to 98 at.%, more in particular from 70 to 96 at.%.

As indicated, one or more copromoters may be present, such as cobalt, but also molybdenum.

The invention also relates to a copper promoted nickel catalyst which also contains cobalt. This catalyst comprises 70 to 96 at.% nickel, based on content of total nickel and total promoters together, the molar copper/cobalt ratio ranging from 0.1 to 10, preferably from 0.3 to 3. If desired, the catalyst further contains 15 to 60 parts by weight of carrier material.

The invention is used for the conversion of alkylnitriles, with the alkyl radical consisting of 2-30 carbon atoms, which radical may be substituted or unsubstituted, may contain one or more unsaturated carbon-carbon bond, and may contain aromatic or aliphatic rings.

According to a preferred embodiment the starting material is composed of saturated and/or unsaturated fatty nitriles derived from fatty acids having 12-22 carbon atoms in the fatty acid chain. The alkyl chains may or may not contain unsaturated carbon-carbon bonds.

The process according to the invention can be carried out continuously, preferably non-cyclically, e.g. in a fixed bed, such as a "trickle phase" reactor, or in a fluidized bed. It is also possible, and this is preferred, to carry out the reaction batchwise. Preferably, this occurs in a "slurry phase".

The reaction conditions, such as temperature, pressure, residence time, use of solvent, amount of catalyst and the like, are determined, inter alia, by the nature of the nitrile to be used and the desired final product.

According to a preferred embodiment of the process, the feed used is substantially only alkylnitrile, which means that no coreactants are used, such as amines, alcohols, ketones and the like Moreover, no solvents will then be used in principle. More in particular, the feed to the reactor consists of 100% alkylnitrile, with the exception of minor amounts of contamination present in technical grade alkylnitrile.

A general tendency is to prevent excessive $NH_3$ partial pressure by removing $NH_3$. The point is that in case of excessive partial pressure of $NH_3$ the formation of secondary amines is suppressed.

Conventional conditions for the reactions are known from the literature and may be maintained in the process according to the invention. Therefore, the reaction temperature preferably ranges from 100° to 300° C., and the $H_2$ pressure preferably ranges from 1 to 50 bar.

According to an embodiment of the process of the invention a two-step process (slurry phase) is used for the preparation of dialkylamines. In the first reaction step the nitrile is completely converted into amines. If desired, also a complete or partial hydrogenation of the unsaturated carbon-carbon bonds occurs in the hydrogenation of unsaturated nitrile.

In the second reaction step condensation and deammonation reactions take place to form the desired dialkylamines.

For the first reaction step, e.g. the following reaction conditions are used:
Temperature: 125°-250° C.
Partial pressure $H_2$: 1-50 bar
Ventilation at intervals or continuously For the second reaction step, e.g. the following reaction conditions are used:
Temperature: 150°-250° C.
Partial pressure $H_2$: 1-15 bar
Ventilation at intervals or continuously For the purpose of this invention ventilation is the refreshment of the gaseous phase present in the reactor so as to keep the $NH_3$ partial pressure sufficiently low. The amount of catalyst is equal in both steps and varies from 0.001 to 5 wt. % (calculated as nickel metal) based on the reaction mixture. It is remarked that the first and second reaction step only differ in reaction conditions, such as temperature and pressure, and that the reactor need not be unloaded between the two consecutive steps.

This invention will hereinbelow be illustrated by some examples which are not intended to be limitative.

EXAMPLES

PERFORMANCE

Using the following procedure, a number of experiments were conducted to compare the activities of different catalysts with each other.

The hydrogenation reaction is carried out in a 1 l autoclave having an internal diameter of 76 mm and being 229 mm in height. The maximum operating pressure of the autoclave is 350 at, and the maximum temperature to be used is 340° C. The reactor is provided with a "dispersimax stirring mechanism" consisting of a turbine stirrer connected to a hollow shaft together with baffles. As soon as the stirring mechanism is started, a lower pressure is formed at the turbine stirring blade, resulting in that gas is drawn into the reactor and dispersed in the liquid.

The temperature of the reactor is adjusted by means of a temperature regulator via an electric heating jacket. The temperature is measured with a thermocouple. The pressure in the autoclave is measured with a manometer.

Introduced into the autoclave are 500 g unsaturated "tallow" nitrile with the powdered (<60 μm) catalyst suspended therein. The tallow nitrile has an iodine number of between 50 and 60, a content of free fatty acids of <0.15 wt. %, a content of amide <0.5 wt. %, and a water content <0.1 wt. %. The amount of catalyst is always chosen such that 17 mmol nickel at an Ni/promoter molar ratio <70/30, or otherwise 24 mmol metal, is present in the reaction mixture. After the reaction mixture has been introduced into the autoclave, the reactor is rinsed thrice with hydrogen by bringing the hydrogen pressure in the reactor at 5 bar and then relieving the pressure. Subsequently, the same procedure is repeated twice, but with rotating stirrer (1400 rpm).

After termination of the rinse procedure the hydrogen pressure in the reactor is increased to 1 at, and at a stirring rate of 1400 rpm the reactor is heated to 150° C. at a rate of about 4° C. per minute. As soon as the desired temperature has been reached, the reaction is started by increasing the hydrogen pressure to 25 bar. The hydrogen pressure is maintained via a continuous supply from a buffer vessel, the temperature and pressure of which are recorded. This renders it possible at any moment to measure the hydrogen consumption and therefore the conversion. Every 15 minutes the reactor is rinsed by reducing the pressure to 1 bar. This is done respectively once with inoperative stirrer and twice with rotating stirrer.

If the measured hydrogen consumption corresponds to the amount theoretically calculated amount for the conversion of 500 g "tallow" nitrile, the hydrogen pressure is decreased to 5 bar and the temperature increased to 190° C.

During this second reaction step carried out at 5 bar hydrogen and 190° C., the resulting ammonia is removed every 30 min. by lowering the pressure from 5 bar hydrogen to 1 bar hydrogen. This step is carried out once with stationary stirrer and twice with rotating stirrer, the pressure each time being brought at 5 bar in the interval.

During the performance of the second reaction step, about 15 ml of the reactor contents are drained off every 30 min. via a sampling tap. This sample is analyzed for the average molecular weight of the mono-, di- and trialkylamines in the reaction mixtures. As soon as the average molecular weight exceeds 485, the reaction is terminated by cooling the reactor to 120° C. and removing the reaction mixture from the autoclave.

On the basis of the resulting analysis data the activity and selectivity of the catalyst are finally determined.

COMPARATIVE EXAMPLE

A nickel catalyst was prepared by precipitation of nickel from a solution of nickel chloride in the presence of a precursor of an alumina carrier and kieselguhr The precipitate was washed with water and then dried at 110° C. The dried filter cake was ground and then calcined in the air at 375° C. Finally, a reduction was carried out at 375° C. in $H_2$.

The resulting product had the following composition:
77.9 wt. % nickel (calculated as the sum of nickel and nickel oxide)
10.3 wt. % alumina
11.8 wt. % silica The BET surface of the product was 200 $m^2/g$, and by means of dynamic $H_2$ chemisorption experiments the specific nickel surface was determined at 64 $m^2/g$ nickel totally present. The pore volume was 0.37 $cm^3/g$ and the helium density 4.19 $g/cm^3$.

This catalyst (A) was used in the process indicated above. The resulting final product had the following composition:
monoalkylamine 5.0 wt. %
dialkylamine 85.6 wt. %
trialkylamine (selectivity) 9.4 wt. %

The catalyst A was physically mixed with a copper-containing catalyst so that the amount of copper approximately equalled 10% of the amount of nickel present. The results of the testing of this mixture are listed in the following table.

| Catalyst | A | mixture A + copper |
|---|---|---|
| Activity (%) | 100 | 100 |
| Monoalkylamine (wt. %) | 5.0 | 5.0 |
| Dialkylamine (wt. %) | 85.6 | 85.7 |
| Trialkylamine (wt. %) | 9.4 | 9.3 |
| Selectivity | 9.4 | 9.3 |

Physically mixing a nickel catalyst and a copper catalyst apparently does not result in an improved yield of dialkylamine. This is caused by the fact that the copper is not in direct contact with nickel, as is the case in the catalyst according to the invention.

EXAMPLE 1

A catalyst B was prepared as described in the Comparative Example, with the understanding that part of the nickel chloride was replaced by copper chloride. The resulting catalyst had the following composition:
77.9 wt. % nickel and copper together (calculated as the sum of metal and metal oxide); molar ratio of nickel:copper=6.1:1
10.3 wt. % alumina
11.8 wt. % silica This catalyst B was used in the process described above. The resulting reaction product had the following composition.
monoalkylamine 5.0 wt. %
dialkylamine 90.5 wt. %
trialkylamine (selectivity) 4.5 wt. %

The activity of this catalyst was about 11% higher than the activity of the catalyst A used in the Comparative Example. Here the activity was defined as the reciprocal value of the time required to arrive at a final product having a content of 5 wt. % monoalkylamine.

A comparison of Example 1 with the Comparative Example clearly shows the higher selectivity of the process according to the invention.

EXAMPLE 2

In the manner as described in Example 1 a catalyst (C) was prepared having the following composition:
77.9 wt. % nickel and copper together (calculated as the sum of metal and metal oxide); molar ratio of nickel:copper=20.6:1
10.3 wt. % alumina
11.8 wt. % silica The results of the testing of the catalysts are listed in the following table:

| Catalyst | A | B | C |
|---|---|---|---|
| Activity % | 100 | 111 | 105 |
| monoalkylamine wt % | 5.0 | 5.0 | 5.0 |
| dialkylamine wt % | 85.6 | 90.5 | 88.7 |
| trialkylamine wt % (selectivity) | 9.4 | 4.5 | 6.3 |
| reaction time (min) | 210 | | |

The activity is defined as in example 1 and expressed as that relative to catalyst A (100 %). These results, too, show the promoting effect of copper with respect to the formation of dialkylamine.

Figure 2:
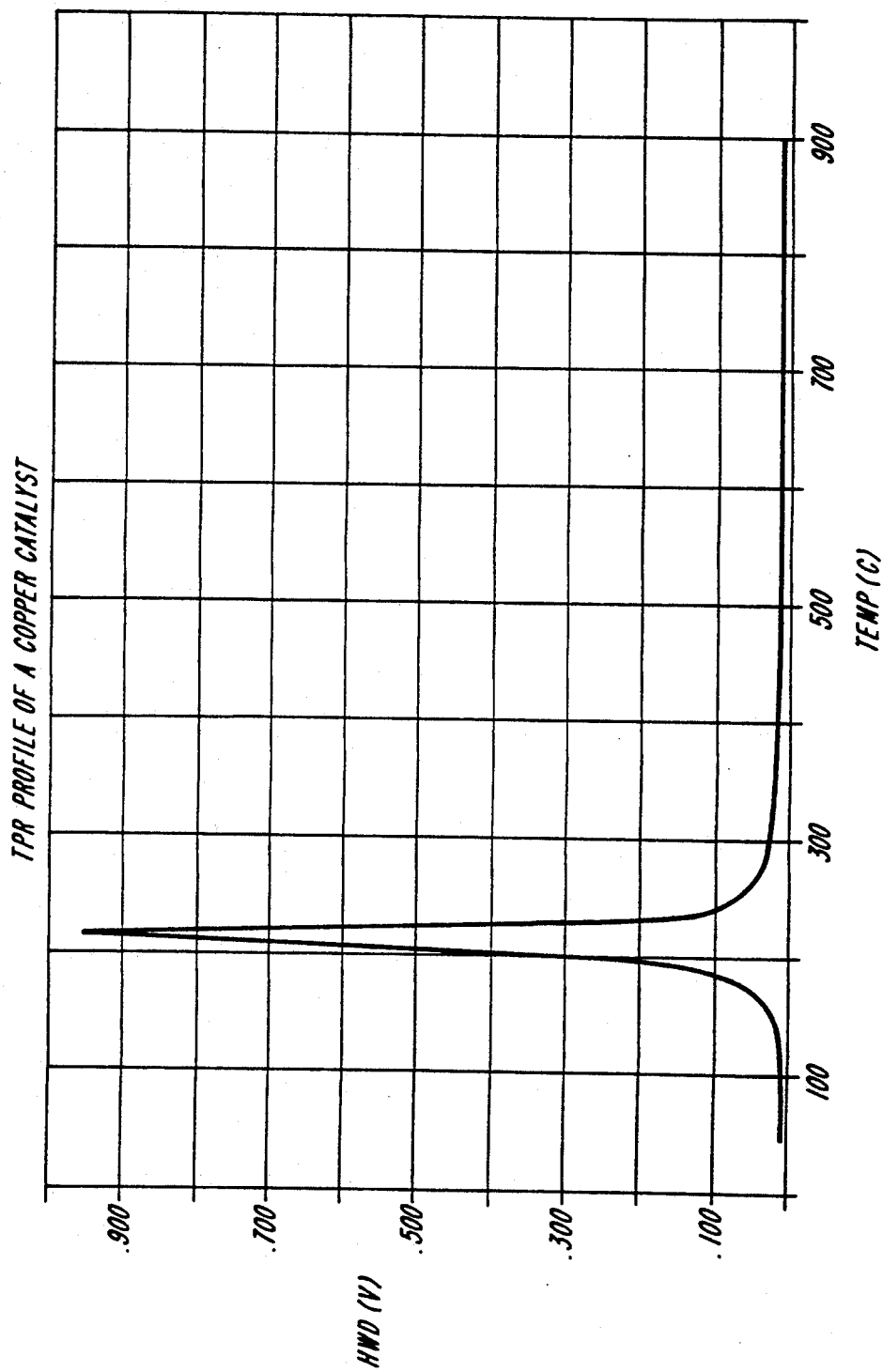
Figure 3:
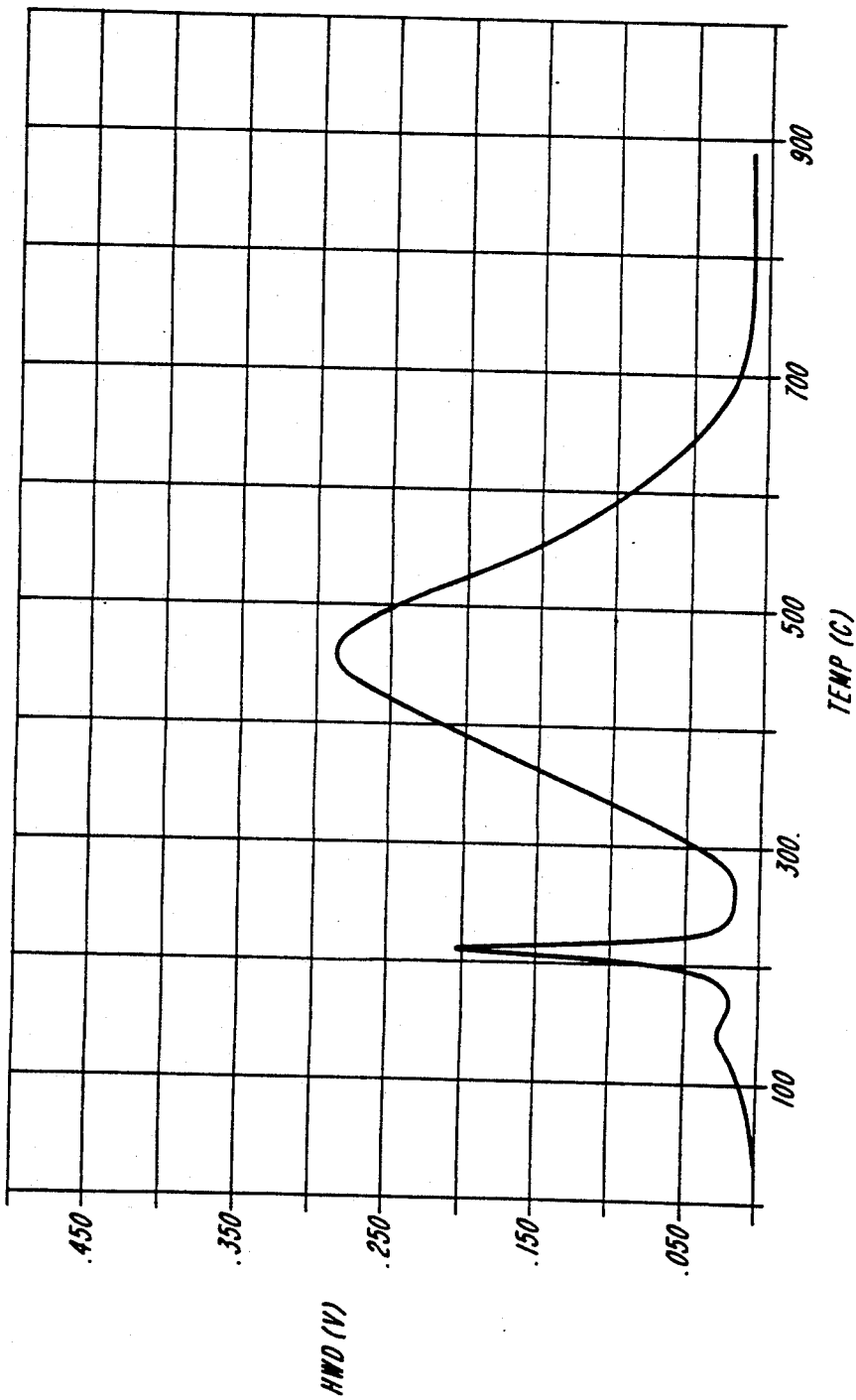
Figure 4:
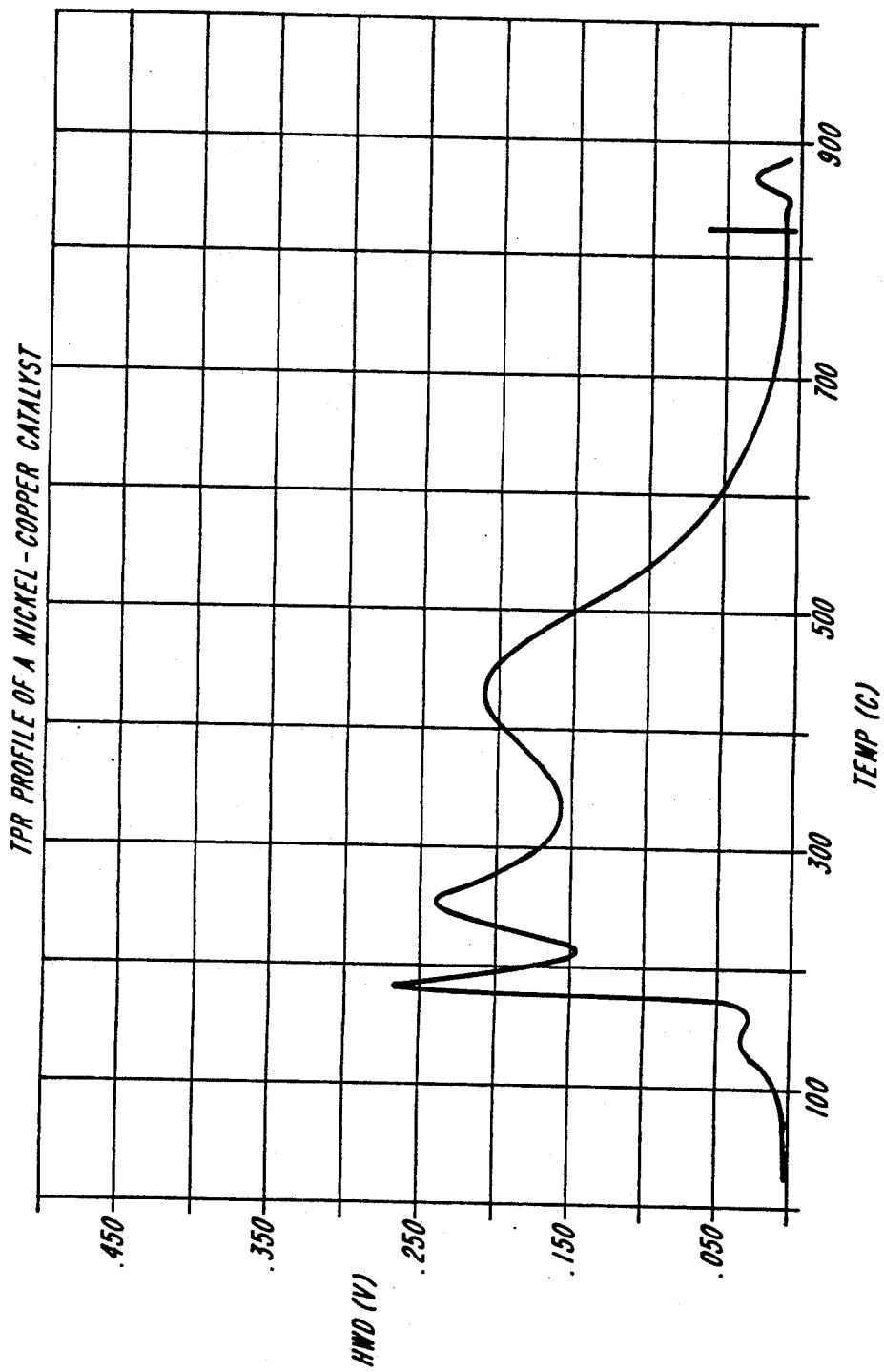

FIG. 1 shows a TPR profile of a nickel catalyst (A) and FIG. 2 a TPR profile of a copper catalyst. The difference in peak maximum is clear: with nickel 470° C. and with copper 220° C. FIG. 3 shows the TPR profile of a physical mixture of a nickel catalyst and a copper catalyst, from which it can be cleary seen that the peaks are at the same positions as for the individual components. FIG. 4, however, shows a TPR profile of a nickel-copper catalyst (catalyst B from Example 1). Characteristic is the middle peak at 260° C., which is caused by the presence of a phase in which nickel and copper are in direct contact with each other. This catalyst with a nickel-copper mixed phase indicates the contemplated improved yield of dialkylamines, as appears from Example 1. It is clear that a catalyst according to the invention should contain a nickel-copper mixed phase.

EXAMPLES 3–6 AND COMPARATIVE EXAMPLE

The catalysts D–G were prepared as described in the Comparative Example with the understanding that part of the nickel chloride was replaced by copper chloride and cobalt chloride. The resulting catalysts had the following composition:

77.9 wt. % nickel, copper, and cobalt (calculated as the sum of metal and metal oxide)
10.3 wt. % alumina
11.8 wt. % silica The total metal content was always constant, the mutual ratios between nickel, copper, and cobalt, however, vary as follows:

| Catalyst | at % Ni | at % Cu | at % Co |
|---|---|---|---|
| D | 90.2 | 9.8 | — |
| E | 85.0 | 9.8 | 5.2 |
| F | 80.0 | 9.5 | 10.5 |
| G | 75.2 | 9.5 | 15.2 |

Catalyst K is a catalyst prepared according to the procedure given in the Comparative Example.

With these catalysts the following results were obtained:

|  | K | D | E | F | G |
|---|---|---|---|---|---|
| monoalkylamine wt % | 5.0 | 5.0 | 5.0 | 5.0 | 5.0 |
| dialkylamine wt % | 85.6 | 90.7 | 90.2 | 90.2 | 90.6 |
| trialkylamine wt % (selectivity) | 8.7 | 5.8 | 4.8 | 4.8 | 4.3 |
| activity (%) | 100 | 114 | 117 | 124 | 137 |
| reaction time (min) | 280 |  |  |  |  |

The selectivity of the above catalysts D–G has been clearly improved as compared with the catalyst K form the Comparative Example, and moreover the presence of cobalt has a positive effect on the activity.

We claim:

1. A process for preparing secondary alkylamine in high yield, comprising the steps of:
providing an alkylamine starting material having an alkyl chain consisting of 2–30 carbon atoms;
providing a catalyst on a carrier material, said catalyst comprising nickel, a copper promoter and, optionally, a second promoter at least a portion of which copper is in direct contact with said nickel as a mixed phase with said nickel, said catalyst containing 70–96 at. % nickel based on the total content of said promoter(s) and nickel, whereby said catalyst has a selectivity not exceeding 8; and
selectively hydrogenating said alkylnitrile starting material in a slurry phase of said material using said catalyst, whereby at least 85% of secondary alkylamine is produced without significant production of tertiary alkylamine.

2. The process of claim 1, wherein in said hydrogenation step said catalyst has a selectivity not exceeding 6.5.

3. The process of claim 1, wherein in said hydrogenation step 5–100% of said copper promoter in said catalyst is in contact with said nickel.

4. The process of claim 1, wherein in said hydrogenation step said catalyst further comprises cobalt as a promoter.

5. The process of claim 1, wherein in said hydrogenation step said carrier forms 5–95 wt. % of said catalyst.

6. The process of 1, wherein in said hydrogenation step said carrier forms 15–60 wt. % of said the catalyst.

7. The process of claim 1, wherein in said hydrogenation step said carrier is selected from the group consisting of $SiO_2$, $Al_2O_3$, and $SiO_2$ and $Al_2O_3$ in combination.

8. The process of claim 1 wherein said step of providing an alkylnitrile starting material further comprises providing a fatty acid and obtaining a fatty nitrile therefrom.

9. The process of claim 1 further comprising the steps of:
providing an unsaturated nitrile starting material; and preparing therefrom a secondary unsaturated amine.

10. The process of claim 1 wherein said steps of providing said alkylnitrile starting material and selectively hydrogenating said provided alkylnitrile nitrile material are carried out batchwise.

11. The process of claim 1 wherein said steps of providing said alkylnitrile starting material and selectively hydrogenating said provided alkylnitrile are carried out continuously and non-cyclically.

12. A process for preparing a secondary fatty acid amine in high yield, comprising the steps of:
providing a fatty nitrile starting material having 12–22 carbon atoms;
providing a catalyst comprising nickel, a copper promoter and, optionally, a second promoter at least a portion of which copper is in direct contact with said nickel as a mixed phase with said nickel, said catalyst containing 70–96 at. % nickel based on the total content of said promoter(s) and nickel, whereby said catalyst has a selectivity not exceeding 8, and further providing a carrier material for supporting said catalyst; and
selectively hydrogenating said fatty nitrile in a slurry phase with said catalyst, whereby at least 85% of secondary fatty acid amine is produced without significant production of tertiary fatty acid amine.

* * * * *

UNITED STATES PATENT AND TRADEMARK OFFICE
CERTIFICATE OF CORRECTION

PATENT NO. : 5,235,108
DATED : August 10, 1993
INVENTOR(S) : Frederik Borninkhof et al.

It is certified that error appears in the above-indentified patent and that said Letters Patent is hereby corrected as shown below:

Column 2, line 46, "$\geq$ 70/30," should read --$\geq$ 70/30,--.

Column 5, line 64, "NH3" should read --$NH_3$--.

Column 6, line 25, "NH3" should read --$NH_3$--.

Column 6, line 65, "< 70/30" should read --$\geq$ 70/30--.

Signed and Sealed this

Twenty-sixth Day of April, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,235,108
DATED : August 10, 1993
INVENTOR(S) : Frederik Borninkhof, et al It is certified that error appears in the above-indentified patent and that said Letters Patent is hereby corrected as shown below:

Claim 1, column 9, line 58, "alkylamine starting material" should read -- alkylnitrile starting material--.

Signed and Sealed this

Sixteenth Day of April, 1996

*Attest:*

BRUCE LEHMAN

*Attesting Officer*   Commissioner of Patents and Trademarks